United States Patent [19]

Hoffman, Jr.

[11] Patent Number: 4,808,595
[45] Date of Patent: Feb. 28, 1989

[54] FUROPYRIDINE SULFONAMIDES AND THEIR OPTHALMOLOGICAL COMPOSITIONS

[75] Inventor: Jacob M. Hoffman, Jr., North Wales, Pa.

[73] Assignee: Merck & Co., Inc., Rahway, N.J.

[21] Appl. No.: 190,319

[22] Filed: May 5, 1988

Related U.S. Application Data

[63] Continuation-in-part of Ser. No. 129,202, Dec. 7, 1987, abandoned, which is a continuation of Ser. No. 946,228, Dec. 24, 1986, abandoned.

[51] Int. Cl.⁴ ................ A61K 31/435; C07D 491/048
[52] U.S. Cl. .................................... 514/302; 514/212; 514/255; 514/233.8; 540/524; 544/127; 544/362; 546/116
[58] Field of Search ............... 546/116; 540/524; 544/127, 362; 514/212, 229, 255, 302

[56] References Cited

U.S. PATENT DOCUMENTS 4,544,667 10/1985 Shephard et al. .................. 514/470

FOREIGN PATENT DOCUMENTS 129478 12/1984 European Pat. Off. .
2081712 6/1981 United Kingdom .

Primary Examiner—Mary C. Lee
Assistant Examiner—Bernard I. Dentz
Attorney, Agent, or Firm—William H. Nicholson; Michael C. Sudol, Jr.

[57] ABSTRACT

Furopyridine sulfonamides are carbonic anhydrase inhibitors useful in the treatment of elevated intraocular pressure and disorders associated therewith such as glaucoma.

12 Claims, No Drawings

FUROPYRIDINE SULFONAMIDES AND THEIR OPTHALMOLOGICAL COMPOSITIONS

This is a continuation-in-part of copending application, Ser. No. 129,202, filed Dec. 7, 1987, now abandoned, which in turn is a continuation of copending application, Ser. No. 946,228, filed Dec. 24, 1986, now abandoned.

SUMMARY OF THE INVENTION

This invention is concerned with novel compounds useful in the treatment of elevated intraocular pressure with the general structural formula:

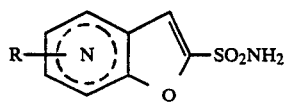

wherein the N indicates that the moiety is a pyrido, dihydropyrido or tetrahydropyrido ring with the nitrogen at the 5 or 6 position.

The invention is also concerned with novel pharmaceutical formulations comprising one of the novel compounds as active ingredient and a method of treating elevated intraocular pressure and disease states associated therewith such as glaucoma.

The invention is further concerned with novel processes for preparing the novel compounds.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e. the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof. European patent publication 129,478 discloses substituted benzo[b]thiophene-2-sulfonamides and U.S. Pat. No. 4,544,667 discloses substituted benzo[b]furan-2-sulfonamides as being useful in the treatment of elevated intracular pressure.

DETAILED DESCRIPTION OF THE INVENTION

The novel compound of this invention has structural formula:

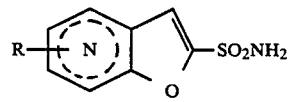

or N-oxide, or an ophthalmologically acceptable salt thereof
wherein:

is a pyrido, dihydropyrido or tetrahydropyrido group with the N at the 4-, 5-, 6- or 7-position; and
R is
(1) $C_{1-5}$ alkyl, either straight chain, branched chain or cyclic such as cyclopropyl and either unsubstituted or substituted with hydroxy, amino, $C_{1-5}$ alkylamino or di($C_{1-5}$ alkyl)amino, the alkyl groups of which can be joined together to form a 5–7-membered heterocycle such as pyrrole, piperidine, morpholine, piperazine or N-methylpiperazine
(2) Hydrogen
(3) —OR$^1$, wherein R$^1$ is hydrogen, $C_{1-5}$ alkyl including cyclopropyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-4}$ alkyl, or $C_{2-4}$ alkanoyl,
(4)

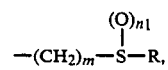

wherein m is 0–3, and n is 0, 1 or 2,
(5) —N(R$^1$)$_2$ wherein the R$^1$ groups can be the same or different, and if lower alkyl, they can be joined together to form a 5–7-membered heterocycle such as pyrrole, piperidine, morpholine, piperazine or N-methylpiperazine,
(6) halo such as chloro, bromo or fluoro,
(7) —NO₂, or
(8) oxo—; and if

represents a dihydro or tetrahydropyrido the N can be substituted with R¹ or —CONH₂.

A preferred embodiment of the novel compound is that wherein

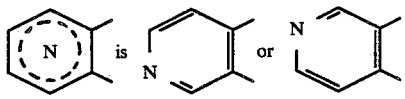

It is also preferred that R be hydrogen, hydroxy, hydroxy-$C_{1-5}$ alkyl, $C_{1-5}$ alkylamino-$C_{1-5}$ alkyl or di($C_{1-5}$ alkyl)amino-$C_{1-5}$alkyl.

The novel processes of this invention comprise derivatization of the intact bicyclic ring systems which are known in the art.

The sulfonamide group, which is present in all of the novel compounds, is introduced by treating the corresponding lithium sulfinate with hydroxylamine-O-sulfonic acid in aqueous sodium acetate at or about room temperature for about 10 to 24 hours.

An alternate procedure comprises adding the corresponding sulfonyl chloride to ice cold ammonium hydroxide.

The pyrido-N-oxides are prepared by treatment with a per acid such as m-chloroperbenzoic acid in an inert organic solvent at about 30°–50° C. over a period of about 10 to 24 hours.

Alternatively, the N-oxides are prepared by oxidation with 30% hydrogen peroxide in acetic acid at about 35°–60° C. for about 18–36 hours.

Compounds carrying an alkylamino group substituted on one of the pyrido carbons are prepared by treating the corresponding chloro-pyrido compound with the alkylamine at about 90°–120° C. for about 3 to 24 hours.

Compounds carrying a hydroxymethyl group may be prepared by treating an N-oxide of a methyl substituted compound with acetic anhydride at about 120° C. to reflux temperature for a few minutes followed by treatment with dilute hydrochloric acid at about 90°–110° C. for about 2 to 6 hours. The foregoing procedure is best performed with the compound in which the sulfonamide is protected as an N,N-dimethylformamidine derivative. This protective group is removed during the process if the dilute hydrochloric acid is 20% HCl. The protective group is maintained if the hydrochloric acid is 6% HCl.

The hydroxymethyl substituent is converted to other desired compounds by procedures such as depicted below.

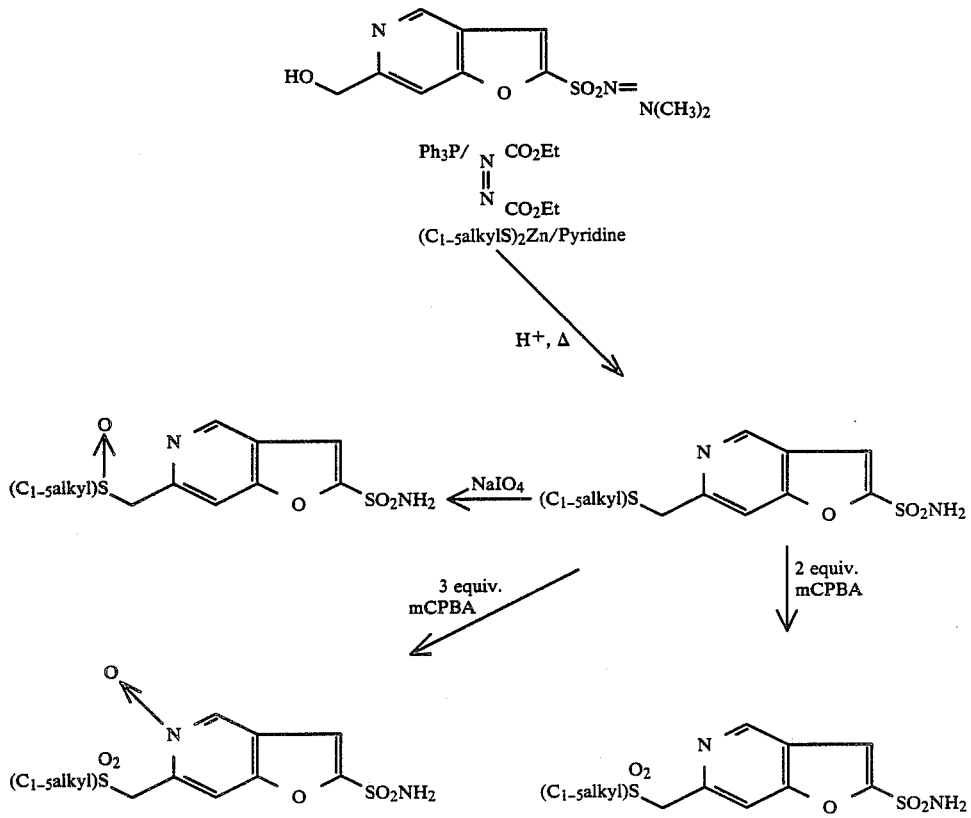

The alkylthiomethyl compound is obtained by adding triphenylphosphine to an ethereal solvent such as THF, ether, or 1,2-dimethoxyethane at about −20° to 0° C. and stirring for about 10 to 30 minutes followed by the addition of diethyl azodicarboxylate followed in about 10 to 30 minutes with the addition of bis (C$_{1-5}$ alkylthio)-zinc and the hydroxymethyl compound. After about 45 minutes at −20° to 0° C., pyridine is added and the mixture is permitted to warm to about −5° to +10° C. over about 4–5 hours followed by standard work-up procedures for Wittig reactions.

The sulfur is subsequently oxidized to sulfoxide with sodium metaperiodate; to the sulfone with 2 equivalents of m-chloroperbenzoic acid; or the sulfone-N-oxide with 3 equivalents of m-chloroperbenzoic acid.

The novel pharmaceutical formulations of this invention are adapted for oral administration such as tablets, capsules for the like; for nasal administration, especially in the form of a spray; for injection, in the form of a sterile injectable liquid; or for topical ocular administration in the form of solutions, suspensions ointments or solid water soluble polymeric inserts.

This invention is particularly concerned with formulations adapted for topical ocular administration for the treatment of glaucoma and other stages of elevated intraocular pressure and contain about 0.1% to 15% by weight of medicament, especially about 0.5 to 2% by weight of medicament, the remainder being comprised of carriers and other excipients well known in the art.

The medicament in the novel topical ocular formulations comprises one of the novel compounds of this invention either alone or in combination with a β-adrenergic blocking agent such as timolol maleate or a parasympathomimetic agent such as pilocarpine. In such combinations the two active agents are present in approximately equal amounts.

The novel method of treatment of this invention comprises the treatment of elevated intraocular pressure by the administration of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

The utility of the novel compounds was determined from the observation that the intraocular pressure (IOP) of the α-chymotrypsinized rabbit eye was significantly lowered by the bilateral instillation of solutions of a representative number of the compounds shown in table I:

TABLE I
EFFECT OF TOPICALLY ADMINISTERED DRUG
ON THE a-CHYMOTRYPSIN-INDUCED ELEVATION
OF IOP IN THE RABBIT[a]

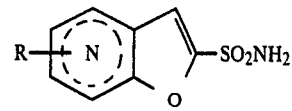

| TEST COMPOUND | DOSE (%)[b] | MAX. IOPw (mm Hg)[c] |
|---|---|---|
| 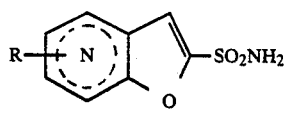 | 0.5% suspension<br>0.1% solution | −7.2<br>−7.2 |
| 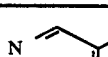 | 0.5% suspension | −5.2 |

TABLE I-continued
EFFECT OF TOPICALLY ADMINISTERED DRUG
ON THE a-CHYMOTRYPSIN-INDUCED ELEVATION
OF IOP IN THE RABBIT[a]

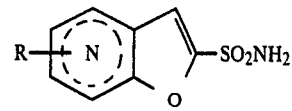

| TEST COMPOUND | DOSE (%)[b] | MAX. IOPw (mm Hg)[c] |
|---|---|---|
| 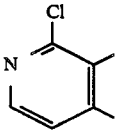 | 0.5% suspension<br>0.1% solution | −7.7<br>−5.7 |
| 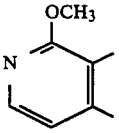 | 0.5% suspension | −4.8 |
| 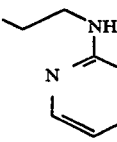 | 0.5% suspension | −3.2 |
| 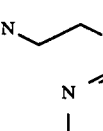 | 0.5% solution | −2.3 |
| 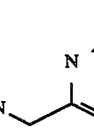 | 0.1% solution | −5.5 |
| 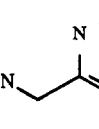 | 0.1% solution | −4.5 |
| 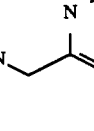 | 0.1% solution | −2.7 |
|  | 0.1% solution | −3.5 |

TABLE I-continued
EFFECT OF TOPICALLY ADMINISTERED DRUG ON THE a-CHYMOTRYPSIN-INDUCED ELEVATION OF IOP IN THE RABBIT[a]

| TEST COMPOUND | DOSE (%)[b] | MAX. IOPw (mm Hg)[c] |
|---|---|---|
| R—[structure with N, SO₂NH₂, O] CH₃S—N(H)—[pyridine structure] | 0.5% solution | −5.7 |

[a] Rabbits were pretreated with a-chymotrypsin at least 1 month previously in right eye only. Compound or vehicle (0.5% HEC) was instilled (50 ml) into both eyes. For full protocol see Sugrue et al, J. Pharm. Exp. Ther., 232, 534 (1985).
[b] A single 50 ml drop of the test compound was applied topically as a formulation of the indicated % concentration in freshly prepared hydroxyethylcellulose (HEC) vehicle.
[c] The reported number is the maximum, statistically significant drop in IOP recorded during the 5 hour duration of the assay.

EXAMPLE 1

2-Sulfamoylfuro[3,2-c]pyridine

To a solution of distilled diisopropylamine (16.2 ml, 0.116 mol) in distilled tetrahydrofuran (115 ml), cooled at −10° C., under a nitrogen atmosphere, was added 1.56M butyl lithium in hexane (75.3 ml, 0.117 mol). After 15 minutes, the solution was cooled to −70° C. and there was added dropwise a solution of furo[3,2-c]pyridine (11.74 g, 0.0987 mol) in tetrahydrofuran (70 ml). With vigorous stirring the gummy precipitate formed a salmon-colored powder. After one hour, sulfur dioxide gas was bubbled over the surface with gradual warming to room temperature. The suspension was diluted with diethyl ether (200 ml) and the precipitate was collected by filtration. This crude lithium sulfinate intermediate (29.1 g) was dissolved in water (200 ml) and sodium acetate trihydrate (61 g, 0.45 mol) and hydroxylamine-O-sulfonic acid (18 g, 0.16 mol) were added. The solution was stirred for 18 hours as the product slowly precipitated. The precipitated product was collected by filtration and redissolved in ethyl acetate/methanol, dried over anhydrous sodium sulfate, filtered through a pad of charcoal and evaporated to give white crystalline product (8.0 g, 41% yield). This material was recrystallized from ethyl acetate/methanol to give 6.7 g, m.p. 216°–218° C.

Analysis calculated for $C_7H_6N_2O_3S$: N-14.14, C-42.41, H-3.05. Found: N-14.15, C-42.50, H-3.03.

EXAMPLE 2

2-Sulfamoylfuro[3,2-c]pyridine-5-oxide

To a warm (40° C.) solution of 2-sulfamoylfuro[3,2-c]pyridine (2.68 g, 13.5 mmol) in methanol (30 ml) and ethyl acetate (10 ml) was added dropwise a solution of m-chloroperbenzoic acid (3.22 g, 15 mmol) in ethyl acetate (13 ml). The reaction mixture was stirred for 18 hours as product precipitated. The pure product was collected by filtration and crystallized from hot dimethyl sulfoxide by dilution with ethanol to give 2.4 g (83% yield), m.p. 247°–248° C.

Analysis calculated for $C_7H_6N_2O_4S$: N-13.08, C-39.25, H-2.82. Found: N-13.06, C-39.52, H-2.85.

EXAMPLE 3

2-Sulfamoyl-4-chloro-furo[3,2-c]pyridine

To a solution of 4-chloro-furo[3,2-c]pyridine (6.17 g, 40.2 mmol) in tetrahydrofuran (80 ml), under a nitrogen atmosphere at −70° C., was added dropwise a solution of 0.7M lithium diisopropylamide in THF (64 ml, 44.8 mmol). After stirring for ½ hour, sulfur dioxide gas was bubbled over the surface of the reaction and the temperature was allowed to gradually rise to room temperature. Dilution with diethyl ether (150 ml) caused the lithium sulfinate intermediate to precipitate. This precipitate (15 g) was collected by filtration and dissolved in water (80 ml). After addition of sodium acetate trihydrate (21.6 g, 0.26 mol) and hydroxylamine-O-sulfonic acid (10.4 g, 0.088 mol), mixture was stirred for 18 hours as the product slowly precipitated. The precipitated crude product was collected by filtration, dissolved in ethyl acetate/methanol. This solution was dried over anhydrous sodium sulfate, filtered through a pad of charcoal and evaporated to give pure crystalline product (5.25 g, 56% yield). Recrystallization of this material from ethyl acetate gave product with m.p. 192°–194° C.

Analysis calculated for $C_7H_5ClN_2O_3S$: N-12.04, C-36.13, H-2.17. Found: N-12.08, C-36.01, H-2.10.

EXAMPLE 4

2-Sulfamoyl-4-(propylamino)furo[3,2-c]pyridine hydrochloride

A solution of 2-sulfamoyl-4-chloro-furo[3,2-c]pyridine (2.09 g, 9.0 mmol) and n-propylamine (7.5 ml, 88 mmol) in ethanol (7.5 ml) was heated in a sealed pressure vessel at 95° C. for 18 hours. The resulting solution was evaporated and the residue was treated with saturated sodium carbonate. The product was extracted into ethyl acetate/methanol, dried over anhydrous sodium sulfate and evaporated. The residue was triturated with diethyl ether to give 1.95 g (85% yield) of product, m.p., 248°–250° C. This material was suspended in diethyl ether (10 ml) and 5N ethanolic hydrogen chloride (4 ml) was added to give, initially, a solution. Dilution with diethyl ether precipitated the salt which was collected by filtration and recrystallized from ethanol to give 1.84 g (70% yield) of the hydrochloride salt, m.p. 247°–249° C.

Analysis calculated for $C_{10}H_{13}N_3O_3S \cdot HCl$: N-14.40, C-41.16, H-4.84. Found: N-14.49, C-41.08, H-4.94.

EXAMPLE 5

2-Sulfamoyl-4-(2-hydroxyethylamino)furo[3,2-c]pyridine

A mixture of 2-sulfamoyl-4-chloro-furo[3,2-c]pyridine (1.75 g, 7.5 mmol) in 2-aminoethanol (5.5 ml, 91 mmol) was heated at 110° C. for 5 hours. This solution was diluted with water and the product was extracted into ethyl acetate. The ethyl acetate extract was evaporated and the residue was triturated with diethyl ether to give solid product (1.48 g). This material was recrystallized from ethyl acetate to give pure product (1.38 g, 71% yield), m.p. 192°–195° C.

Analysis calculated for $C_9H_{11}N_3O_4S$: N-16.23, C-42.01, H-4.31. Found: N-16.42, C-42.25, H-4.36.

EXAMPLE 6

2-Sulfamoyl-4-methoxyfuro[3,2-c]pyridine

To a solution of 4-methoxyfuro[3,2-c]pyridine (4.69 g, 31.5 mmol) in tetrahydrofuran (45 ml), under a nitrogen atmosphere at −70° C., was added dropwise 1.6M butyl lithium in hexane (22.5 ml, 36 mmol). After ½ hour, sulfur dioxide gas was bubbled over the reaction surface and the mixture was allowed to warm to room temperature. After addition of diethyl ether (50 ml) the precipitated lithium sulfinate intermediate was collected by filtration. This salt (7.1 g) was dissolved in water (45 ml) and sodium acetate trihydrate (15.3 g, 0.112 mol) and hydroxylamine-O-sulfonic acid (3.8 g, 33.5 mmol) were added. After stirring for 5 hours, the precipitated product was collected (4.3 g) and recrystallized from ethyl acetate to give pure product (4.0 g, 56% yield), m.p. 180°–182° C.

Analysis calculated for $C_8H_8O_4S$: N-12.20, C-42.10, H-3.53. Found: N-12.39, C-42.41, H-3.60.

EXAMPLE 7

2-Sulfamoylfuro[3,2-c]pyridin-4(5H)-one

To a suspension of furo[3,2-c]pyridin-4(5H)-one (2.7 g, 20 mmol) in tetrahydrofuran (40 ml), under a nitrogen atmosphere and at −70° C., was added 0.7M lithium diisopropylamide in THF (72 ml, 50 mmol). This mixture was stirred for 1 hour and sulfur dioxide gas was bubbled over the reaction surface while gradually warming to room temperature. This suspension was diluted with diethyl ether and the precipitated lithium sulfinate intermediate was collected by filtration. This material (8.2 g) was dissolved in water (45 ml) and sodium acetate trihydrate (18 g, 0.132 mol) and hydroxylamine-O-sulfonic acid (5.0 g, 0.44 mol) were added. After stirring for 18 hours, the precipitated product was collected by filtration, washed with ethanol and diethyl ether to give 1.49 g (34.8% yield), m.p. 286°–289° C. The product can be recrystallized from a large volume of hot methanol.

Analysis calculated for $C_7H_6N_2O_4S$: N-13.08, C-39.26, H-2.83. Found: N-13.02, C-39.46, H-2.88.

Alternate Procedure: A suspension of 2-sulfamoyl-4-methoxyfuro[3,2-c]pyridine (0.75 g, 3.3 mmol) in 10% aqueous hydrochloric acid (40 ml) was heated at 100° C. for 4½ hours. Upon cooling, the product precipitated and was collected by filtration, washed with ethanol and diethyl ether to give 0.53 g (76% yield), m.p. 286°–289° C.

EXAMPLE 8

2-Sulfamoylfuro[2,3-c]pyridine

The title compound was prepared according to the procedure described for the preparation of 2-sulfamoyl-furo[3,2-c]pyridine except furo[2,3-c]pyridine was substituted for furo[3,2-c]pyridine. This compound was obtained in 40% yield after recrystallization from ethyl acetate, m.p. 199°–201° C.

Analysis calculated for $C_7H_6N_2O_3S$: N-14.14, C-42.41, H-3.05. Found: N-14.20, C-42.48, H-3.03.

EXAMPLE 9

2-Sulfamoyl-7-methoxyfuro[2,3-c]pyridine

Step A: Preparation of 7-methoxyfuro[2,3-c]pyridine

Sodium methoxide was prepared by dissolution of sodium pellets (2.8 g, 0.122 mol) in methanol (75 ml). After complete dissolution, the methanol solvent was evaporated under vacuum. 7-Chloro-furo-[2,3-c]pyridine (10.25 g, 66.8 mmol) was dissolved in dry dimethylformamide (75 ml) and added in one portion to the prepared sodium methoxide solution under a nitrogen atmosphere. This solution was heated at 110° C. for 1½ hours as the by-product sodium chloride precipitated. The reaction was diluted with water and extracted with diethyl ether. This ethereal solution was dried over anhydrous sodium sulfate, evaporated to dryness and the residue was distilled under vacuum to give 5.6 g (56% yield) of product, b.p. 88°–89° C./4.5 mm Hg.

Step B: Preparation of 2-sulfamoyl-7-methoxyfuro[2,3-c]pyridine

The title compound was prepared according to the procedure described for the preparation of 2-sulfamoyl-4-methoxyfuro[3,2-c]pyridine (Example 6) except that 7-methoxyfuro[2,3-c]pyridine was substituted for 4-methoxyfuro[3,2-c]pyridine. This compound was obtained in 64% yield after recrystallization from ethyl acetate, m.p. 204°–206° C.

Analysis calculated for $C_8H_8N_2O_4S$: N-12.28, C-42.10, H-3.53. Found: N-12.30, C-42.29, H-3.49.

EXAMPLE 10

2-Sulfamoylfuro[2,3-c]pyridin-7(6H)-one

To a partial suspension of furo[2,3-c]pyridin-7(6H)-one (1.62 g, 12 mmol) in tetrahydrofuran (40 ml), under a nitrogen atmosphere at −30° C., was added dropwise 1.56M butyl lithium in hexane (16.6 ml, 26 mmol). After stirring at −20° C. for ½ hour, sulfur dioxide gas was bubbled over the reaction surface with gradual warming to room temperature. The reaction was diluted with diethyl ether (50 ml) and glacial acetic acid (0.74 ml, 12 mmol), and the precipitated lithium sulfinate intermediate was collected by filtration. This material (4.2 g) was dissolved in water (40 ml) and sodium acetate trihydrate (5.5 g, 41 mmol) and hydroxylamine-O-sulfonic acid (1.54 g, 13 mmol) were added. After stirring for 18 hours, the precipitated product was collected by filtration and crystallized from methanol to give 1.1 g (43% yield) of pure product, m.p. 290°–291° C.

Analysis calculated for $C_7H_6N_2O$: N-13.08, C-39.25, H-2.82. Found: N-13.26, C-39.50, H-2.82.

EXAMPLE 11

2-Sulfamoyl-4-[2-(dimethylamino)ethylamino]furo[3,2-c]pyridine dihydrochloride A mixture of 2-sulfamoyl-4-chloro-furo[3,2-c]pyridine (1.02 g, 4.4 mmol) in 2-(dimethylamino)ethylamine (1.4 ml, 12.8 mmol) was warmed at 90° C. for 8 hours. The cooled mixture was diluted with water and made basic with saturated sodium carbonate. The product was extracted into ethyl acetate/methanol, dried over anhydrous sodium sulfate, and filtered. The solution was evaporated to give crude product. This residue was dissolved in methanol and excess ethanolic HCl was added. After dilution with diethyl ether, the resultant gum was digested in ethanol to give a powder (0.86 g, 55% yield), mp: 275°–278° C. Recrystallization of this salt by dissolution in a minimum amount of warm water and subsequent dilution with ethanol gave pure dihydrochloride salt (0.56 g) mp: 281°–283° C.

Analysis calculated for $C_{11}H_{16}N_4O_3S \cdot 2HCl$: N-15.68, C-36.98, H-5.08. Found: N-15.92, C-37.24, H-5.42.

EXAMPLE 12

2-Sulfamoyl-6-methylfuro[3,2-c]pyridine

Step A: Preparation of 6-Methylfuro[3,2-c]pyridin-4(5H)-one

To a solution of 3-(2-furanyl)methacrylic acid (15.2 g, 0.10 mol) and triethylamine (14.2 ml, 0.10 mol) in dry acetone (200 ml), cooled at 0° C. under a nitrogen atmosphere, was added dropwise a solution of ethyl chloroformate (9.9 ml, 0.104 mol) in acetone (25 ml). After stirring this mixture for 1.5 hours, a solution of sodium azide (11.3 g, 0.174 mol) in water (45 ml) was added dropwise. After an additional 1 hour, this mixture was poured into ice/water and the resultant acylazide was extracted into benzene (250 ml). The benzene layer was washed with water, dried over anhydrous sodium sulfate and then filtered through a pad of charcoal. This solution was added dropwise to a mixture of diphenylmethane (150 ml) and tri-n-butylamine (28 ml) which was previously heated to 220° C. The addition rate was adjusted so as to maintain the pot temperature above 200° C. as the benzene flash distilled. Upon completion of the addition (2.5 hours), the reaction was allowed to cool to room temperature as the product crystallized. After dilution of this mixture with diethyl ether the crystalline solid was collected by filtration to give analytically pure product (12.35 g, 80% yield), mp: 234°–237° C.

Analysis calculated for $C_8H_7NO_2$: N-9.39, C-64.42, H-4.73. Found: N-8.99, C-64.33, H-4.70.

Step B: Preparation of 4-Chloro-6-methylfuro[3,2-c]pyridine

A mixture of 6-methylfuro[3,2-c]pyridin-4(5H)-one (11.9 g, 0.08 mol) and phosphorus oxychloride (15.2 ml, 0.163 mol) was heated, under a nitrogen atmosphere, at 100° C. for 1.5 hours. The cooled blackish liquid was poured onto crushed ice and the solution made basic with sodium hydroxide solution. The precipitated product was extracted into methylene chloride. This solution was dried over anhydrous sodium sulfate, filtered through a pad of charcoal and evaporated. Pure product was collected by filtration after the residue was triturated with hexane to give 12.9 g (96% yield), mp: 64.5°–66° C.

Analysis calculated for $C_8H_6ClNO$: N-8.36, C-57.33, H-3.61. Found: N-8.63, C-57.65, H-3.68.

Step C: Preparation of 6-Methylfuro[3,2-c]pyridine

To a solution of 4-chloro-6-methylfuro[3,2-c]pyridine (12.98 g, 0.0776 mol) in glacial acetic acid (160 ml) under a nitrogen atmosphere was added zinc powder (7.0 g, 0.107 mol.). This mixture was heated at 110° C. for 2.5 hours and then filtered hot to remove zinc. The acetic acid solution was evaporated and the residue dissolved in water and made strongly basic by addition of sodium hydroxide. The zinc salts were filtered and washed thoroughly with methylene chloride. The aqueous filtrate was extracted with methylene chloride and the combined washings were dried over anhydrous sodium sulfate, filtered through a charcoal pad and the solvent evaporated to give 9.5 g (87% yield) of pure product, mp: 55°–56° C.

Analysis calculated for $C_8H_7NO$: N-10.52, C-72.16, H-5.30. Found: N-10.82, C-72.01, H-5.51.

Step D: Preparation of 2-Sulfamoyl-6-methylfuro[3,2-c]pyridine

To a solution of distilled diisopropylamine (7.6 ml, 59 mmol) in distilled tetrahydrofuran (60 ml), under a nitrogen atmosphere and cooled to −70° C., was added 1.6M butyl lithium in hexane (34.4 ml, 55 mmol). After stirring for 0.5 hour a solution of 6-methylfuro[3,2-c]pyridine (6.66 g, 50 mmol) in tetrahydrofuran (50 ml) was added dropwise. After stirring 1.5 hours, sulfur dioxide gas was bubbled over the reaction surface to give a tan precipitate. The reaction mixture was allowed to warm to room temperature and then diluted with diethyl ether and the precipitate collected by filtration. This lithium sulfinate salt (17.6 g) was air dried and then dissolved in water (90 ml). Sodium acetate trihydrate (29 g, 0.21 mol) and hydroxylamine-o-sulfonic acid (11.5 g, 0.10 mol) were added and the solution was stirred at room temperature for 20–25 hours as the product precipitated. This product was filtered and dissolved in ethyl acetate/methanol, dried over anhydrous sodium sulfate, and filtered through a charcoal pad. The evaporated residue was triturated with diethyl ether to give nearly pure product (5.19 g, 49% yield). Recrystallization from hot ethyl acetate containing a little methanol to effect initial dissolution afforded pure product, mp 233°–234.5° C.

Analysis calculated for $C_8H_8N_2O_3S$: N-13.20, C-45.27, H-3.80. Found: N-13.02, C-45.28, H-3.91.

EXAMPLE 13

2-Sulfamoyl-6-hydroxymethylfuro[3,2-c]pyridine

Step A: Preparation of N,N-Dimethyl-N'(6-methylfuro[3,2-c]pyridine-2-sulfonyl)formamidine To a suspension of 2-sulfamoyl-6-methylfuro[3,2-c]pyridine (3.65 g, 17.2 mmol) in acetonitrile (80 ml), under a nitrogen atmosphere, was added N,N-dimethylformamide dimethyl acetal (2.6 ml, 19.6 mmol). This reaction was stirred for 1.5 hours at room temperature and then diluted with chloroform and washed with water. The organic layer was separated, dried over anhydrous sodium sulfate, filtered through a charcoal pad and the solvent evaporated. The residue was triturated with diethyl ether and the product collected (4.31 g, 93% yield) and used as is. A small portion was crystallized from ethyl acetate for microanalysis, mp. 175°–177° C.

Analysis calculated for $C_{11}H_{13}N_3O_3S$: N-15.72, C-49.42, H-4.90. Found: N-15.78, C-49.66, H-5.04.

Step B: Preparation of N,N-Dimethyl-N'-(5-oxido-6-methylfuro[3,2-c]pyridine-2-sulfonyl)formamidine To a solution of N,N-dimethyl-N'-(6-methylfuro[3,2-c]pyridine-2-sulfonyl)formamidine (5.61 g, 21 mmol) in chloroform (65 ml) was added dropwise a solution of commercial 80% pure m-chloroperbenzoic acid (5.0 g, 23 mmol) in chloroform (45 ml). The reaction was stirred for 20 hours and then concentrated on a rotary evaporator to near dryness. The residue was digested in diethyl ether and the precipitated product filtered. This solid (6.06 g) was digested in ethyl acetate/chloroform/methanol and then cooled and pure product collected by filtration (5.76 g, 97% yield), m.p. 248°–249° C.

Analysis calculated for $C_{11}H_{13}N_3O_4S$: N-14.83, C-46.63, H-4.62. Found: N-14.70, C-46.46, H-4.49.

Step C: Preparation of 2-Sulfamoyl-6-hydroxymethylfuro[3,2-c]pyridine

A mixture of N,N-dimethyl-N'-(5-oxido-6-methylfuro[3,2-c]pyridine-2-sulfonyl)formamidine (3.96 g, 14 mmol) in acetic anhydride (12 ml), under a nitrogen atmosphere was heated at 140° C. for 15 minutes to give a dark brown solution. The reaction was cooled to 100° C. and 20% aqueous hydrochloric acid (40 ml) was added and heat was maintained at this temperature for 4 hours. The cooled reaction was carefully made basic with sodium carbonate solution and then exhaustively extracted with ethyl acetate/methanol to isolate product. This extract was dried over sodium sulfate, filtered through a charcoal pad and solvent evaporated to give, after trituration of the residue with diethyl ether, nearly pure product (1.39 g, 43% yield). Recrystallization from hot ethanol afforded pure product (1.14 g), mp 222°–223° C.

Analysis calculated for $C_8H_8N_2O_4S$: N-12.28, C-42.10, H-3.53. Found: N-12.57, C-42.09, H-3.51.

EXAMPLE 14

2-Sulfamoyl-7-methylfuro[3,2-c]pyridine

Step A: Preparation of 7-Methylfuro[3,2-c]pyridin-4-(5H)-one

The title compound was prepared according to the procedure described for 2-sulfamoyl-6-methylfuro[3,2-c]pyridin-4-(5H)-one (Example 12 Step A) except 3-(2-furanyl)-3-methylacrylic acid was substituted for 3-(2-furanyl)methacrylic acid. Title compound was obtained in 41% yield, m.p. 239°–241° C., after crystallization from methanol.

Analysis calculated for $C_8H_7NO_2$: N-9.39, C-64.42, H-4.73. Found: N-9.43, C-64.65, H-4.83.

Step B: Preparation of 4-chloro-7-methylfuro[3,2-c]pyridine

The title compound was prepared according to the procedure described for 4-chloro-6-methylfuro[3,2-c]pyridine (Example 12, Step B) except 7-methylfuro[3,2-c]pyridin-4-(5H)-one was substituted for 6-methylfuro[3,2-c]pyridin-4-(5H)-one. Title compound was obtained in 98% crude yield and used as is. A portion was crystallized from cold diethyl ether for microanalysis, mp. 51.5°–53° C.

Analysis calculated for $C_8H_6NO$: N-8.36, C-57.33, H-3.61. Found: N-8.32, C-57.34, H-3.71.

Step C: Preparation of 7-Methylfuro[3,2-c]pyridine

The title compound was prepared according to the procedure described for 6-methylfuro[3,2-c]pyridine (Example 12, step C) except 4-chloro-7-methylfuro[3,2-c]pyridine was substituted for 4-chloro-6-methylfuro[3,2-c]-pyridine. Title compound was obtained pure in 81% yield after distillation under vacuum, b.p. 74° C./2.2 mm Hg. This material crystallized, m.p. 41°–43° C.

Analysis calculated for $C_8H_7NO$: N-10.52, C-72.16, H-5.30. Found: N-10.59, C-71.89, H-5.27.

Step D: Preparation of 2-Sulfamoyl-7-methylfuro[3,2-c]pyridine

To a solution of 7-methylfuro[3,2-c]pyridine (1.33 g, 10 mmol) in distilled tetrahydrofuran (20 ml), under a nitrogen atmosphere and cooled to −70° C., was added dropwise 0.7M lithium diisopropylamide in tetrahydrofuran (15.5 ml, 11 mmol) to give a gummy precipitate. After stirring for 0.5 hour, sulfur dioxide gas was bubbled over the reaction surface to give a white precipitate. After slowly warming this mixture to room temperature, hexane was added and the precipitate collected by filtration. This precipitate was washed with diethyl ether and air dried. The resultant lithium sulfinate salt (3.5 g) was dissolved in water (25 ml) and sodium acetate trihydrate (8.2 g, 60 mmol) and hydroxylamine-O-sulfonic acid (2.33 g, 20 mmol) were added. After stirring for 20 hours, the precipitated product was collected by filtration, then dissolved in ethyl acetate/methanol, dried over anhydrous sodium sulfate and filtered through a charcoal pad. The resultant solution was evaporated and the residue triturated with diethyl ether to give solid product (1.24 g, 58% yield). Recrystallization from ethyl acetate gave 1.1 g, m.p. 179.5°–181.5° C.

Analysis calculated for $C_8H_8N_2O_3S$: N-13.20, C-45.27, H-3.80. Found: N-13.38, C-44.94, H-3.84.

EXAMPLE 15

2-Sulfamoyl-6-(dimethylaminomethyl)furo[3,2-c]pyridine

Step A: Preparation of 6-methylfuro[3,2-c]pyridine-N-oxide Monohydrate

To a solution of 6-methylfuro[3,2-c]pyridine (9.05 gm, 68 mmol) in chloroform (120 mL) was added commercial 80% pure m-chloropenbenzoic acid (16.1 g, 7.5 mmol). The solution was stirred at 25° C. for 2.5 hours and then diluted with an equal volume of chloroform and washed twice with saturated sodium carbonate solution, and once with brine. This solution was dried over anhydrous sodium sulfate, filtered and evaporated to dryness. The residue was triturated with diethyl ether and the purified product was collected by filtration to give 5.82 g (57% yield), mp: 76°–79° C. Some product was also isolated as dihydrate mp: 84°–85° C.

Analysis calculated for $C_8H_7NO_2 \cdot H_2O$: N,-8.38; C,-57.48; H,-5.43. Found: N,-8.46; C,-57.06; H,-5.31.

Also analysis calculated for $C_8H_7NO_2 \cdot 2H_2O$: N,-7.57; C,-51.89; H,-5.98. N,-7.08; C,-52.12; H,-5.90.

Step B: Preparation of 6-hydroxymethylfuro[3,2-c]pyridine

A mixture of 6-methylfuro[3,2-c]pyridine-N-oxide monohydrate (19.85 g, 0.119 mol) in acetic anhydride (30 mL) was heated at 100° C. for one half hour. Then the reaction mixture was diluted with 20% hydrochloric acid (100 mL) and heating was continued for one hour. The solution was cooled and made basic with sodium hydroxide solution. The product was extracted into chloroform, dried over anhydrous sodium sulfate, filtered through a pad of charcoal and evaporated. The residue was triturated with cool benzene and the crystalline product collected by filtration to give 11.36 g (64% yield), mp: 72°–74° C.

Analysis calculated for $C_8H_7NO_2$: N,-9.39; C,-64.42; H,-4.73. Found: N,-9.40; C,-64.38; H,-4.79.

Step C: Preparation of 6-(dimethylaminomethyl)furo[3,2-c]pyridine

To a solution of triethylamine (3.45 mL, 24.7 mmol) in methylene chloride (16 mL) under a nitrogen atmosphere and cooled below 5° C. was added p-toluenesulfonyl chloride (4.65 g, 24.4 mmol) in one portion. After stirring the mixture for 15 minutes, a solution of 6- hydroxymethylfuro[3,2-c]pyridine (2.68 g, 18 mmol) in methylene chloride (18 mL) was added dropwise. By tlc the reaction was complete in 6–8 hours. Dimethylamine gas was bubbled over the reaction surface until product formation was complete. The reaction solution was washed with water and the product extracted into dilute hydrochloric acid. The acidic aqueous extract was made basic with sodium hydroxide solution and the product extracted into diethyl ether. The ethereal solution was dried over anhydrous sodium sulfate, filtered through a pad of charcoal and evaporated to give an oil (1.76 g). The oil was distilled under vacuum to give 1.56 g (49% yield) of pure product, bp: 93°–94° C./1.6 mm Hg. Upon standing the product crystallized, mp: 42°–44° C.

Analysis calculated for $C_{10}H_{12}N_2O$: N, 15.90, C, 68.15, H, 6.87. Found: N, 15.74, C, 68.03, H, 6.79.

Step D: Preparation of 2-sulfamoyl-6-(dimethylaminomethyl)furo[3,2-c]pyridine

To a solution of 6-(dimethylaminomethyl)furo[3,2-c]pyridine (2.11 g, 12 mmol) in dry tetrahydrofuran (25 mL), under a nitrogen atmosphere and cooled below −70° C., was added dropwise 0.7M lithium diisopropylamide in tetrahydrofuran (19 mL, 13.3 mmol) to give a gummy precipitate. After one half hour, sulfur dioxide gas was bubbled over the reaction surface to give a whitish precipitate. The mixture was warmed gradually to room temperature and then diluted with diethyl ether to completely precipitate the intermediate sulfinate salt. This crude sulfinate salt (4.88 g) was dissolved in water (30 mL) and sodium acetate trihydrate (14.85 g, 109 mmol) and hydroxylamine-o-sulfonic acid (4.15 g, 36.7 mmol) were added. After stirring at room temperature for 10–20 hours, the reaction solution was made weakly basic (pH 7.5) and the partially precipitated product was extracted into 5% methanol/ethyl acetate. This solution was dried over anhydrous sodium sulfate, filtered and evaporated. The residue was triturated with diethyl ether and the precipitated product (2.49 g, 81% yield) collected by filtration. A portion (667 mg) of this material was crystallized by dissolution in methanol/ethyl acetate and boiling off the methanol to give pure product (504 mg), mp: 249°–251° C. The hydrochloride salt was obtained by treating the free base (1.52 g) with ethanolic hydrogen chloride. This salt was recrystallized from ethanol twice to give 1.12 g, mp: 221°–224° C.

Analysis calculated for $C_{10}H_{13}N_3O_3S$: N, 16.46, C, 47.04, H, 5.13. Found: N, 16.43, C, 47.29, H, 5.47.

Analysis calculated for $C_{10}H_{13}N_3O_3S \cdot HCl$: N, 14.40, C, 41.16, H, 4.84. Found: N, 14.42, C, 41.08, H, 4.89.

Employing the procedures substantially as described in Example 15, substituting for the dimethylamine used in Step C, an equivalent amount of an amine of formula $R^2R^3NH$ as defined in Table II there are prepared the furopyridinesulfonamides also depicted in Table II:

TABLE II

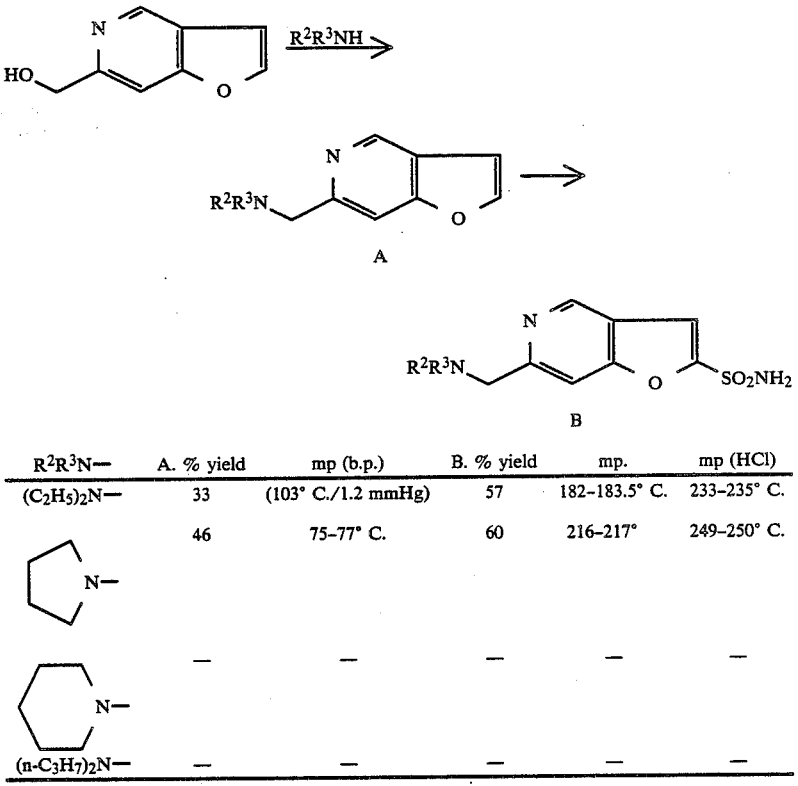

| $R^2R^3N-$ | A. % yield | mp (b.p.) | B. % yield | mp. | mp (HCl) |
|---|---|---|---|---|---|
| $(C_2H_5)_2N-$ | 33 | (103° C./1.2 mmHg) | 57 | 182–183.5° C. | 233–235° C. |
| ⟨pyrrolidinyl⟩N— | 46 | 75–77° C. | 60 | 216–217° | 249–250° C. |
| ⟨piperidinyl⟩N— | — | — | — | — | — |
| $(n-C_3H_7)_2N-$ | — | — | — | — | — |

EXAMPLE 16

2-Sulfamoyl-6-(isobutylaminomethyl)furo[3,2-c]pyridine

Step A: Preparation of N,N-Dimethyl-N'-[6-(hydroxymethyl)furo[3,2-c]pyridine-2-sulfonyl]formamidine N,N-Dimethylformamide dimethyl acetal (1.0 ml, 0.007 mole) was added dropwise (10 minutes) to a suspension of 6-hydroxymethyl-2-sulfamoylfuro[3,2- c]pyridine (1.33 g, 0.005% mole) in acetonitrile (25 ml). The mixture was stirred at room temperature under $N_2$ for 40 hours. The reaction mixture was diluted with $CHCl_3$ and washed with water. The organic phase was separated, dried ($Na_2SO_4$) and filtered through charcoal. The filtrate was concentrated to dryness and the residue recrystallized from ethyl acetate to give the product as a yellow solid 0.8 g (48% yield). Recrystallization from methanol/ethyl acetate gave an analytical sample, mp: 161°–163° C.

Analysis Calculated for $C_{15}H_{13}N_3O_4S$ C, 46.63, H, 4.63, M, 14.83. Found: C, 47.00, H, 4.67; M, 15.20.

Step B: Preparation of N,N-Dimethyl-N′-[6-formylfuro[3,2-c]pyridine-2-sulfonyl]formamidine A mixture of N,N-dimethyl-N′-[6-(hydroxymethyl)-furo[3,2-c]pyridine-2-sulfamoyl]-formamidine (7.4 g, 0.026 mole) and activated manganese dioxide (14 g, 0.16 mole) in $CHCl_3$ (250 ml) was stirred at reflyx under $N_2$ for 2 hours. A second portion of manganese dioxide (6 g) was added and the mixture heated at reflux for 2 hours. After addition of a third portion of manganese dioxide (2 g) and heating at reflux for another 30 minutes, the reaction mixture was filtered and the filtrate concentrated to dryness. The residual solid was taken up in $CHCl_3$ (100 ml) and after addition of activated $MnO_2$ (1 g), the reaction mixture was heated at reflux for 30 minutes; additional portions of $MnO_2$ (total 2.0 g) were added as the mixture was heated at reflux for 3 hours. The warm mixture was filtered and the residue washed with fresh $CHCl_3$; the filtrate was concentrated in vacuo. Recrystallization of the crude product from methanol-ethyl acetate gave 3.39 g (46% yield) of pale yellow crystalline solid, mp 186°–188° C.

Analysis Calculated for $C_{11}H_{11}N_3O_4S$ C, 46.97; H, 3.94; N, 14.94. Found: C, 47.23; H, 4.05; N, 14.77.

Step C: Preparation of 2-Sulfamoyl-6-(isobutylaminomethyl)furo[3,2-c]pyridine A mixture of N,N-dimethyl-N′-[6-formylfuro[3,2-c]pyridine-2-sulfamoyl]formamidine (1.68 g, 0.006 mole) and isobutylamine (7.3 g, 0.10 mole) in absolute ethanol (60 ml) was stirred at room temperature under $N_2$ for 20 hours. Sodium borohydride (0.25 g, 0.0065 mole) was added and the mixture stirred at room temperature for 6 hours: a second portion of $NaBH_4$ (0.125 g) was added. After stirring for 5 hours, the reaction mixture was concentrated in vacuo and the residue was taken up in water. The aqueous solution was acidified with dilute aq. HCl, extracted with ethyl acetate and treated with aq. $NH_4OH$ (to pH 9) to give a white solid precipitate. Recrystallization of the product from methanol-ethyl acetate gave 1.15 g (68% yield) of white crystalline solid, mp 233°–235° C. (dec).

Analysis Calculated for $C_{12}H_{17}N_3O_3S$ C, 50.87; H, 6.04; N, 14.83. Found: C, 51.06; H, 6.10; N, 15.04.

A methanol solution of this amine was treated with ethanolic HCl and the solution concentrated to dryness. Recrystallization of this product from methanol/isopropanol gave a white crystalline solid, mp 239°–241° C. (dec).

Analysis Calculated for $C_{12}H_{17}N_3O_3S$ C, 45.07; H, 5.67; N, 13.14. Found: C, 44.68; H, 5.78; N, 13.33.

EXAMPLE 17

2-Sulfamoyl-6-(methylthioethylaminomethyl)furo[3,2-c]pyridine

Step A: Preparation of 6-[2-(1,3-Dioxolanyl)]furo[3,2-c]pyridine

A mixture of 6-formylfuro[3,2-c]pyridine (2.45 g, 0.017 mole), ethylene glycol (3.0 g, 0.048 mole) and p-toluenesulfonic acid monohydrate (0.8 g, 0.0042 mole) in benzene (100 mL) was heated at reflux with stirring under $N_2$ for 7 hours. The reaction mixture was cooled, poured into aqueous $NaHCO_3$ and extracted with diethyl ether. The ether extracts were combined, washed with water and brine and dried over anhydrous $Na_2SO_4$. Filtration and evaporation gave a yellow oily residue, which was purified by flash chromatography on a silica gel column using 5% acetone-$CH_2Cl_2$ as eluant. The product obtained as a yellow oil, was distilled to give 2.2 g (69% yield) of colorless oil, bp 132°–137° C./3 mm Hg.

Analysis Calculated for $C_{10}H_9NO_3$ C, 62.82; H, 4.74; N, 7.33. Found: C, 63.15; H, 5.02; N, 7.35.

Step B: Preparation of 2-Sulfamoyl-6-[2-(1,3-dioxolanyl)]furo[3,2-c]pyridine n-Butyllithium solution (3.8 ml, 1.6M in hexane) was added to a well stirred solution of diisopropylamine (0.6 g, 0.006 mole) in tetrahydrofuran (10 mL) at $< -30°$ C. and under $N_2$. After stirring at $< -50°$ C. for 20 minutes, a solution of 6-[2-(1,3-dioxolanyl)]furo[3,2-c]pyridine (0.95 g, 0.005 mole) in tetrahydrofuran (10 ml) was added dropwise (15 minutes) and the reaction mixture stirred at $< -65°$ C. for 2 hours. Gaseous sulfur dioxide was introduced over the surface of the mixture for about 10 minutes. The reaction mixture was stirred at room temperature for 30 minutes, diluted with ether and filtered to collect a yellow solid which was washed with ether and air-dried. The solid was added to water (25 ml), followed by the addition of sodium acetate trihydrate (3.0 g, 0.022 mole) and hydroxylamine O-sulfonic acid. This aqueous solution was stirred at room temperature for about 18 hours. The aqueous mixture was filtered to collect the yellow solid product and the filtrate was extracted with 15% methanol-ethyl acetate. Concentration of the extracts gave an additional quantity of crude product. Purification was accomplished by flash chromatography on a silica gel column using 5% $CH_3OH$—$CH_2Cl_2$ as eluant. The isolated product was recrystallized from ethyl acetate to give 0.47 g (35% yield) of white crystalline solid. mp. 191°–193° C.

Analysis. Calculated for $C_{10}H_{10}N_2O_5S$: C, 44.44; H, 3.73; N, 10.37. Found: C, 44.28; H, 3.51; N, 10.31.

Step C: Preparation of 2-Sulfamoyl-6-formylfuro[3,2-c]pyridine

A solution of conc HCl (10 ml) in water (15 ml) was added slowly to a well stirred solution of 2-sulfamoyl-6-[2-(1,3-dioxolanyl)]furo[3,2-c]pyridine (0.95 g, 0.0035 mole) in tetrahydrofuran (50 ml). The reaction mixture was heated at reflux for 3 hours, cooled and concentrated in vacuo. The residue was taken up in aq $NaHCO_3$ and extracted with ethyl acetate. The ethyl acetate extracts were combined, washed with brine and dried over $Na_2SO_4$. Filtration and evaporation gave a residue which was triturated with ether. The product obtained was recrystallized from ethyl acetate to give 0.65 g (82% yield) of pale yellow crystalline solid, mp: 187° C. dec.

Analysis calculated for $C_8H_6N_2O_4S$ C, 42.48, H, 2.67, N, 12.38. Found: C, 42.70, H, 2.37, N, 12.41.

Step D: Preparation of 2-Sulfamoyl-6-(methylthioethylaminomethyl)furo[3,2-c]pyridine A mixture of 2-sulfamoyl-6-formylfuro[3,2-c]pyridine (0.62 g, 0.0027 mole) and methylthioethylamine (1.8 g, 0.02 mole) in absolute ethanol was heated at 50° C. for 2 hours and stirred at room temperature overnight (16 hours) under $N_2$. Sodium borohydride (0.1 g, 0.0026 mole) was added and the reaction mixture stirred at room temperature for 4 hours; a second portion of sodium borohydride (25 mg) was added and stirring was continued for 3 hours. The reaction mixture was concentrated in vacuo and the residue taken up in aq HCl and extracted with ethyl acetate. The aqueous solution was treated with conc. $NH_4OH$ (to pH 9) to give a white solid precipitate. Recrystallization of the product from methanol-ethyl acetate gave 0.63 g (76% yield) of white crystalline solid, mp 212°-214° C. dec. A methanol solution of the amine was treated with ethanolic HCl and the mixture concentrated in vacuo. Recrystallization of the residue from methanol-isopropanol gave a white solid, mp 239°-241° C. dec.

Analysis Calculated for $C_{11}H_{15}N_3O_3S_2HCl$ C, 39.11; H, 4.77, N, 12.44. Found: C, 39.02; H, 4.65, N, 12.43.

Alternate Procedure

A mixture of N,N-dimethyl-N'-[6-formylfuro[3,2-c]pyridine-2-sulfamoyl]formamidine (1.55 g, 0.0055 mole) and methylthioethylamine (2.4 g, 0.026 mole) in absolute ethanol was heated at 50° C. for 2 hours. An additional quantity of methylthioethylamine (0.6 g) was added and the reaction mixture heated at 50° C. for 6 hours and stirred at room temperature overnight. Sodium borohydride (2.4 g, 0.0062 mole) was added and the mixture stirred at room temperature for 3 hours; a second portion (50 mg) of sodium borohydride was added and stirring was continued for one hour. The reaction mixture was concentrated in vacuo and the residue was taken up in aq HCl and extracted with ethylacetate. The aqueous solution was treated with conc. $NH_4OH$ (to pH 9) to give a pale yellow precipitate. Recrystallization from methanol-ethyl acetate gave 1.3 g (78% yield) of product as a white solid, mp 212°-214° C. dec.

Analysis Calculated for $C_{11}H_{15}N_3O_3S_2$ C, 43.84; H, 5.02; N, 13.94. Found: C, 43.69; H, 4.75; N, 13.87.

EXAMPLE 18

2-Sulfamoyl-6-(methylsulfinylethylaminomethyl)-furo[3,2-c]pyridine

Sodium metaperiodate (0.28 g, 0.0013 mole) was added to a mixture of 2-sulfamoyl-6-(methylthioethylaminoethyl)furo[3,2-c]pyridine (0.36 g, 0.0012 mole) in methanol (45 ml) and water (12 ml) and the reaction mixture stirred at room temperature under $N_2$ for 4 hours; a second portion of $NaIO_4$ (30 mg) was added and stirring was continued for 3 hours. The reaction mixture was filtered to remove precipitated $NaIO_3$ and the filtrate was concentrated in vacuo. The residue was purified by flash chromatography on a silica gel column using 30% methanol —$CH_2Cl_2$ as eluant. The product, obtained as a yellow solid, was taken up in methanol and treated with ethanolic HCl. The solution was concentrated in vacuo and the residue was recrystallized from methanol-ethanol to give a 0.25 g (60% yield) of pale yellow crystalline solid, mp 208°-210° dec.

Analysis Calculated for $C_{11}H_{15}N_3O_4S_2.HCl$ C, 37.34; H, 4.56; N, 11.88. Found: C, 37.00; H, 4.32; N, 11.69.

EXAMPLE 19

2-Sulfamoyl-6[2-(dimethylamino)ethyl]furo[3,2-c]pyridine

Step A: Preparation of N,N-diethyl-2-methylfuran-3-carboxamide

To a solution of 2-methyl-3-furoic acid (34.75 g, 0.3469 mol) in dry methylene chloride (200 ml) under an argon atmosphere, were added a catalytic amount of dimethylformamide followed by dropwise addition of oxalyl chloride (45.5 ml, 0.5216 mol). After the addition the reaction mixture was allowed to stir until the effervescence had subsided (4.0 hours). The excess oxalyl chloride/methylene chloride was evaporated and the residue was dissolved in methylene chloride (200 ml). The solution was cooled (ice/acetone) and diethylamine (75.0 ml, 0.725 mol) in methylene chloride (100 ml) was added dropwise. After the addition (1.0 hour) the reaction was poured into ice/water and the solution was acidified to a pH of 3.0. The mixture was extracted with diethyl ether (4×200 ml). The combined extracts were washed with saturated sodium carbonate solution (2×50 ml), water (4×50 ml), brine (2×25 ml), and dried ($MgSO_4$). Solvent evaporation gave 59.75 g of crude product. The oil was distilled to give 52.45 g (83% yield) of product which crystallized upon standing (bp: 91° C./1.2 mmHg; mp 32°-34° C.).

Step B: Preparation of 6-[2-(dimethylamino)ethyl]furo[3,2-c]pyridine-4(5H)-one To a solution of 2,2,6,6-tetramethylpiperidine (5.1 ml, 30.4 mmole) in dry tetrahydrofuran (60 ml), cooled at −78° C. (dryice/acetone) under an argon atmosphere, was added dropwise n-butyllithium (17.3 ml, 27.6 mmole). After the addition the reaction was warmed to −10° C. (ice/acetone). To this solution was added N,N-diethyl-2-methylfuran-3-carboxamide (5.0 g, 27.6 mmole) in tetrahydrofuran (15 ml). After stirring this mixture for 1.0 hour, 3-(dimethylamino)propionitrile (3.27 ml, 29.0 mmole) was added dropwise. The reaction was allowed to warm overnight. The reaction was poured into ice/water and acidified to a pH 3.25 with hydrochloric acid. The mixture was then extracted with diethyl ether (3×150 ml). The pH of the aqueous layer was adjusted to 13.0 using sodium hydroxide solution (40%) and this solution was extracted exhaustively using methylene chloride (10×150 ml). The combined extracts were washed with water (2×50 ml), brine (2×100 ml) and dried ($MgSO_4$). After solvent evaporation 8.25 g of an oil was obtained. This was purified by flash chromatography using 15% methanol/chloroform as the eluting solvent to give analytically pure product (4.65 g, 82% yield), mp: 97.5°-98.0° C. Some starting amide (1.05 g) was recovered from the initial diethyl ether extracts.

Analysis Calculated for $C_{11}H_{14}N_2O_2$: N, 13.59; C, 64.06; H, 6.84. Found: N, 13.26; C, 64.44; H, 7.04.

Step C: Preparation of 4-Chloro-6-[2-(dimethylamino)ethyl]furo[3,2-c]pyridine A mixture of 6-[2-(dimethylamino)ethyl]furo[3,2-c]pyridin-4(5H)-one (3.9 g, 18.9 mmole) and phosphorus oxychloride (5.0 g, 32.6 mmole) was heated, under an argon atmosphere, at 110° C. for 2.0 hours. The cooled blackish liquid was poured onto crushed ice and the solution made basic with sodium hydroxide solution. The alkaline mixture was extracted into methylene chloride (4×100 ml). The combined extracts were washed with water (1×25 ml), brine (2×25 ml) and dried (MgSO4). Solvent removal gave 4.0 g of an oil (88%, yield). The compound was used as is in the following step. A small sample was purified further using a preparative thin layer chromatography plate and eluting with a 25% methanol/74% chloroform/1.0% ammonium hydroxide mixture. The sample was removed from the plate using methylene chloride and treated with excess hydrogen chloride in ethanol. The ethanol was removed via vacuum and the resulting clear oil triturated with diethyl ether to give white crystals, mp: 212°–213° C.

Analysis calculated for $C_{11}H_{13}ClN_2O.2HCl$ N, 9.41; C, 44.39; H, 5.15. Found: N, 9.48; C, 44.42; H, 5.08.

Step D: Preparation of 6-[2-(dimethylamino)ethyl]furo[3,2-c]-pyridine

To a solution of 4-chloro-6-[2-(dimethylamino)ethyl]-furo[3,2-c]pyridine (4.0 g, 16.6 mmole) in glacial acetic acid (50 ml) under an argon atmosphere was added zinc powder (10.85 g, 166.6 mmol). This mixture was heated at 80° C. for 20 minutes and then filtered hot to remove excess zinc. The acetic acid solution was evaporated and the residue dissolved in water and made basic by the addition of sodium hydroxide. The zinc salts were filtered and washed thoroughly with methylene chloride. The aqueous filtrate was extracted with methylene chloride and the combined extracts were dried over magnesium sulfate. The mixture was filtered and the solvent removed to give 3.0 g of an oil. The oil was distilled to yield 2.8 g (89%) of product (bp, 95° C./0.8 mm Hg). A small sample was converted to the dihydrochloride salt using ethanolic hydrochloric acid. The ethanol was removed under vacuum to give a clear oil which upon trituration with diethyl ether gave white crystals mp, 223°–224° C. (dec).

Analysis calculated for $C_{11}H_{14}N_2O.2HCl$: N, 10.65; C, 50.20; H, 6.13. N, 10.41; C, 49.96; H, 6.28.

Step E: Preparation of 2-Sulfamoyl-6-[2-(dimethylamino)ethyl]furo[3,2-c]pyridine To a solution of diisopropylamine (1.8 ml, 12.6 mmole) in dry tetrahydrofuran (25 ml), under an argon atmosphere and cooled to −70° C., was added 1.6M butyllithium in hexane (7.1 ml, 12.2 mmole). After stirring for 0.25 hour a solution of 6-[2-(dimethylamino)ethyl]furo[3,2-c]pyridine (2.0 g, 10.5 mmole) in dry tetrahydrofuran (10 ml) was added dropwise. After stirring 0.25 hour, sulfur dioxide gas was blown over the reaction surface to give a tan precipitate. The reaction was allowed to warm to room temperature and diluted with diethyl ether. The precipitate was collected by filtration. The lithium sulfinate salt was dissolved in water (25 ml). Sodium acetate (1.73 g, 21 mmole) and hydroxylamine-o-sulfonic acid (1.78, 15.75 mmole) were added and the solution was stirred at room temperature for 60 hours. The reaction pH was adjusted to 8.0 with sodium carbonate and the resulting mixture extracted exhaustively with ethyl ethyl acetate. The combined extracts were washed with water (1×50 ml), brine (2×50 ml), and dried using magnesium sulfate. Solvent removal yielded 2.1 g of an impure solid. Flash chromatography using gradient elution (5–15% methanol/chloroform) yielded 1.1 g of product. This product was recrystallized from ethyl acetate/methanol to give 820 mg (28% yield) of a white crystalline solid (mp 157°–160° C.). A sample was treated with ethanolic hydrogen chloride to give pure dihydrochloride salt, mp: 204°–205° C. dec.

Analysis calculated for $C_{11}H_{15}N_3O_3S$: N, 15.61; C, 49.05; H, 5.61. Found: N, 15.46; C, 49.02; H, 5.79.

Analysis calculated for $C_{11}H_{15}N_3O_3S2HCl$: N, 12.28; C, 38.60; H, 5.01. Found: N, 12.09; C, 38.58; H, 4.75.

Employing the procedure substantially as described in Example 19, but substituting for the dimethylaminopropiontrite used in Step B, an equivalent amount of the nitrile of formula $R^2R^3$—N—$(CH_2)_n$—CN, described in Table III there are produced the furopyridine-sulfonamides also described in Table III:

TABLE III

[Structure A: furan with (CH₃CH₂)₂N-C(=O)- group and CH₃, converting to structure with HN-C(=O), R²R³N-(CH₂)ₙ substituent on furo-pyridinone]

[Structure B: chloro-furopyridine with R²R³N-(CH₂)ₙ substituent]

[Structure C: furo[3,2-b]pyridine with R²R³N-(CH₂)ₙ substituent]

[Structure D: 2-sulfamoyl furo[3,2-b]pyridine with R²R³N-(CH₂)ₙ substituent, SO₂NH₂ group]

| R²R³N— | n | A. % yield | mp (°C.) | B. % yield | mp (°C.) | C. % yield | mp (bp) (°C.) | D. % yield | mp (°C.) |
|---|---|---|---|---|---|---|---|---|---|
| (C₂H₅)N— | 2 | 62 | 88–90 | 95 | 157–160(HCl) | 85 | 222–224(2HCl) | 16 | 173–175 |
| (n-C₃H₂)₂N— | 2 | 78 | 100–101 | 90 | 201–210(HBr) | 64 | (136/1.1 mmHg) | 30 | 135–136.5 |
| piperidino-N— | 2 | 52 | 127–129 | 98 | 231–233(HCl) | 87 | 255–257(2HCl) | 19 | 171–174 |
| (CH₃)₂N— | 3 | 98 | 90–91 | 67 | 180°(1.9 HCl) | 92 | 269–270(2HCl) (113–115/1.0 mmHg) | 25 | 190–191 223.5–224.5(HCl) |
| pyrrolidino-N— | 3 | 89 | 102–103 | 62 | 187–189(1.35 HCl) | 62 | (145–140/1.4 mmHg) | 34 | 202–203 |
| (CH₃)₂N— | 4 | 63 | 100–101 | 89 | | 68 | (129–132/.9 mmHg) | 32 | 172–173 |
| CH₃— | 4 | 60 | 131–132 | 88 | | 74 | (80–85/.9 mmHg) 108–110(HCl) | 26 | 1301–131 |

EXAMPLE 20

2-Sulfamoylfuro[3,2-b]pyridine

To a solution of furo[3,2-b]pyridine (1.7 g, 14.3 mmol) in tetrahydrofuran (15 mL) cooled to −30° C., under a nitrogen atmosphere, was added dropwise 1.6M n-butyllithium (10 mL, 16.0 mmol) to give a gummy precipitate which solidified upon cooling to −70° C. After 15 minutes, sulfur dioxide gas was bubbled over the reaction surface to give a gray-colored precipitate. Upon warming to room temperature, the reaction mixture was diluted with diethyl ether and the precipitate was collected by filtration. This crude sulfinate salt (2.85 g) was partially dissolved in water (20 mL) and sodium acetate trihydrate (8.17 g, 60 mmol) and hydroxylamine-o-sulfonic acid (2.26 g, 20 mmol) were added. After stirring for 10–20 hours, the precipitated product was collected by filtration and redissolved in ethyl acetate/methanol. This solution was filtered through charcoal and evaporated. The residue was triturated with diethyl ether to give 1.58 g of product (56% yield). This material was recrystallized from ethylacetate/methanol by boiling off the methanol solvent to give 1.37 g, mp: 219°–221° C.

Analysis calculated for $C_7H_6N_2O_3S$: N, 14.14; C, 42.41; H, 3.05. Found: N, 14.09; C, 42.67; H, 2.98.

EXAMPLE 21

2-Sulfamoylfuro[3,2-b]pyridine-4-oxide

To a suspension of 2-sulfamoylfuro[3,2-b]pyridine (647 mg, 3.27 mmol) in glacial acetic acid (8 mL) was added 30% hydrogen peroxide (0.6 mL). This suspension was warmed at 60° C. for four hours to give a clear solution. Upon cooling the reaction mixture and adding water the product crystallized out. This pure product (444 mg, 63.5% yield) was collected by filtration, washed with water, ethanol and diethyl ether, mp: 236°–237° C. (decomposition).

Analysis calculated for $C_7H_6N_2O_4S$: N, 13.08; C, 39.25; H, 2.82. Found: N, 13.02; C, 39.59; H, 2.91.

EXAMPLE 22

2-Sulfamoyl-6-(diethylaminomethyl)furo[3,2-b]pyridine

Step A: Preparation of ethyl furo[3,2-b]pyridine-6-carboxylate

To a solution of conc. hydrogen chloride (100 mL) containing zinc chloride (11.6 g, 83 mmoL) was added 3-(t-butoxycarbamoyl)furan (13.8 g, 75.4 mmol). After stirring for 5 minutes, the reaction mixture was diluted with ethanol (60 mL) and a solution of ethoxycarbonylmalonaldehyde (11.6 g, 80.6 mmol) in ethanol (40 mL) was added. This mixture was warmed at 80° C. for two hours and then cooled and poured into ice/water and made basic with ammonium hydroxide. The product was extracted into methylene chloride, dried over anhydrous sodium sulfate, filtered through a pad of charcoal and evaporated. This residue was chromatographed on silica gel eluting with chloroform to give 5.92 g of purified product. Crystallization from hexane provided product with, mp: 63°-65° C.

Analysis calculated for $C_{10}H_9NO_3$: N, 7.33; C, 62.82; H, 4.74. Found: N, 7.23; C, 63.09; H, 4.87.

Step B: Preparation of furo[3,2-b]pyridine-6-carboxylic acid

A suspension of ethyl furo[3,2-b]pyridine-6-carboxylate (4.5 g, 23.5 mmol) in 1.25M sodium hydroxide (24 mL) was warmed at 60° C. for one hour to give a clear solution. This solution was cooled, filtered through charcoal and made weakly acidic with conc. hydrogen chloride. The precipitated product was extracted into a large volume of diethyl ether/methanol, dried over anhydrous sodium sulfate, filtered and the solvents removed in vacuo. The residue was triturated with ethanol/diethyl ether and collected to give 3.66 g (95% yield), mp: 238°-239° C.

Analysis calculated for $C_8H_5NO_3$: N, 8.59; C, 58.90; H, 3.09. Found: N, 8.53; C, 58.84; H, 3.10.

Step C: Preparation of N,N-Diethyl furo[3,2-b]pyridine-6-carboxamide

To a suspension of furo[3,2-b]pyridine-6-carboxylic acid (3.26 g, 20 mmol) in dry acetone (40 mL), under a nitrogen atmosphere and cooled in an ice bath, was added dropwise triethylamine (3.1 mL, 22.3 mmol). After 15 minutes, a solution of ethyl chloroformate (2.1 mL, 22.3 mmol) in dry acetone (12 mL) was added dropwise. This solution was stirred for two hours and then diethylamine (4.2 mL, 40.6 mmol) was added. After another hour the reaction mixture was diluted with chloroform/water and the chloroform layer separated and washed with sodium carbonate solution and then 10% hydrochloric acid. The chloroform solution was dried over anhydrous sodium sulfate, filtered through a charcoal pad and evaporated to give crude oily product (4.2 g). This material was purified by fractional distillation to give 2.42 g (55.5% yield) of oil, bp: 155°-156° C./1.2 mmHg.

Step D: Preparation of 6-(diethylaminomethyl)furo[3,2-b]pyridine

To a solution of N,N-diethyl furo[3,2-b]pyridine-6-carboxamide (2.4 g, 11 mmol) in tetrahydrofuran (15 mL), under a nitrogen atomosphere at room temperature, was added 1.0M borane.THF (38.5 mL, 38.5 mmol). This solution was stirred for 1.5 hours and then warmed to 60° C. for 1.5 hours. After cooling to room temperature, acetic acid (2.2 mL, 38.5 mmol) was added to quench excess borane and the reaction mixture was partitioned between methylene chloride and 10% hydrochloric acid. The acid layer was separated and made basic with sodium hydroxide solution and the oily product was extracted into methylene chloride. This solution was dried, filtered and the solvent evaporated to give 1.85 g of crude product. This oil was purified by treatment with ethanolic hydrogen chloride to give the dihydrochloride salt. Upon recrystallization from isopropanol 1.28 g of product salt (42% yield), mp: 214°-216° C., was obtained. Treatment with sodium hydroxide regenerated quantitatively the oily free base.

Analysis calculated for $C_{12}H_{16}N_2O.2HCl$: N, 10.11; C, 51.99; H, 6.54. Found: N, 9.98; C, 51.72; H, 6.32.

Step E: Preparation of 2-sulfamoyl-6-(diethylaminomethyl)furo[3,2-b]pyridine

To a solution of 6-(diethylaminomethyl)furo[3,2-b]pyridine (1.21, 5.94 mmol) in dry tetrahydrofuran (11 mL), under a nitrogen atmosphere and cooled to −70° C., was added dropwise 1.6M butyllithium in hexane (4.2 mL, 6.7 mmol) to give a dark solution. After one hour, sulfur dioxide gas was bubbled over the reaction surface to give a light yellow precipitate. This mixture was allowed to warm to room temperature and diluted with diethyl ether (15 mL). The crude sulfinate salt (1.9 g) was collected by filtration and redissolved in water (11 mL). Sodium acetate trihydrate (3.1 g, 23 mmol) and hydroxylamine-o-sulfonic acid (1.11 g, 10 mmol) were added. This solution was stirred for 15 hours and then the solution was made basic (pH-8.5) with sodium hydroxide and the product was extracted into ehtyl acetate. This solution was dried over anhydrous sodium sulfate, filtered through a pad of charcoal and the solvent evaporated. The residue was triturated with diethyl ether to give crude product (0.73 g). Recrystallization from ethyl acetate gave pure product (551 mg, 33% yield), mp: 189°-190.5° C. A portion of this material was treated with ethanolic hydrogen chloride to give the pure hydrochloride salt after recrystallization from ethanol, mp: 232°-234° C. (decomposition).

Analysis calculated for $C_{12}H_{17}N_3O_3S$: N, 14.83; C, 50.86; H, 6.05. Found: N, 14.65; C, 50.60; H, 5.80.

Analysis calculated for $C_{12}H_{17}N_3O_3S.HCl$: N, 13.14; C, 45.06; H-5.68. Found: N, 13.14; C, 45.01; H-5.52.

EXAMPLE 23

2-Sulfamoylfuro[2,3-b]pyridine-5-carboxylic acid

Step A: Preparation of furo[2,3-b]pyridine-2,5-dicarboxylic acid

A suspension of diethyl furo[2,3-b]pyridine-2,5-dicarboxylate (10.5 g, 40 mmol) in 1N sodium hydroxide (100 mL) was warmed at 70° C. for two hours. The cooled solution was acidified with conc. hydrochloric acid and the precipitate was collected by filtration and successively washed with water, ethanol and diethyl ether to give pure product (8.14 g, 98.5% yield) mp: >315° C.

Analysis calculated for $C_9H_5NO_5$: N, 6.76; C, 52.18; H, 2.43. Found: N, 6.63; C, 51.95; H, 2.21.

Step B: Preparation of furo[2,3-b]pyridine-5-carboxylic acid

A suspension of furo[2,3-b]pyridine-2,5-dicarboxylic acid (5.35 g, 25.9 mmol) in quinoline (40 mL) containing copper dust (2.5 g) was heated under a nitrogen atmosphere at 200° C. for one hour. The cooled mixture was diluted with chloroform and filtered to remove suspended material. The product was extracted into sodium carbonate solution. This solution was carefully acidified with conc. hydrochloric acid and the precipitated product isolated by filtration. This material was dissolved in a large volume of diethyl ether/methanol, dried over anhydrous sodium sulfate and filtered through a pad of charcoal. The solvents were removed in vacuo and the residue triturated with diethyl ether to give pure product (2.68 g, 63% yield), mp: 274°–275° C.

Analysis calculated for $C_8H_5NO_3$: N, 8.59; C, 58.90; H, 3.09. Found: N, 8.53; C, 58.55; H, 2.99.

Step C: Preparation of 2-sulfamoylfuro[2,3-b]pyridine-5-carboxylic acid

To a suspension of furo[2,3-b]pyridine-5-carboxylic acid (1.8 g, 11 mmol) in dry tetrahydrofuran (45 mL), under a nitrogen atmosphere and cooled to −70° C., was added diisopropylamine (1.54 mL, 11 mmol) to give a partial solution. Then 1.6M butyl lithium in hexane (19.7 mL, 31.5 mmol) was added dropwise to give a yellow precipitate. This suspension was stirred for 2.5 hours and then sulfur dioxide gas was bubbled over the reaction surface to give a very thick precipitate. After warming to room temperature, the reaction mixture was diluted with diethyl ether (50 mL) and glacial acetic acid (0.63 mL, 11 mmol) was added. This precipitate was collected by filtration and rinsed with diethyl ether. The hydroscopic sulfinate salt was dissolved in water (43 mL) and sodium acetate trihydrate (12.4 g, 92 mmol) and hydroxylamine-o-sulfonic acid (3.46 g, 30.6 mmol) were added. After stirring for 12–20 hours, the partial suspension was acidified with conc. hydrochloric and after stirring for several hours, the precipitated product was collected by filtration. This crude product (2.2 g) was recrystallized twice from ethanol/methanol (1:1) to give pure product (1.51 g, 57% yield), mp: 307°–308° (decomposition).

Analysis calculated for $C_8H_6N_2O_5S$: N, 11.57; C, 39.67; H, 2.50. Found: N, 11.52; C, 39.68; H, 2.43.

EXAMPLE 24

2-Sulfamoylfuro[2,3-b]pyridine

A suspension of 2-sulfamoylfuro[2,3-b]pyridine-5-carboxylic acid (726 mg, 3.0 mmol) in quinoline (5 mL) containing copper dust (0.5 g) was heated under a nitrogen atmosphere at 225° C. for 3.5 hours. After cooling the reaction mixture to room temperature, chloroform and dilute sodium hydroxide solution were added. This biphasic mixture was filtered through a filter aid pad to remove black suspended material and then the basic aqueous layer was separated and acidified with conc. hydrochloric acid. The product was extracted into ethyl acetate which was dried over anhydrous sodium sulfate and filtered through a pad of charcoal. The residue obtained after removal of the solvent in vacuo was triturated with diethyl ether to give crude product (291 mg). This material was recrystallized from ethyl acetate to give pure product (250 mg, 42% yield), mp: 222°–223° C.

Analysis calculated for $C_7H_6N_2O_3S$: N, 14.14; C, 42.41; H, 3.05. Found: N, 14.32; C, 42.73; H, 2.93.

EXAMPLE 25

2-Sulfamoyl-5-(diethylaminomethyl)furo[2,3-b]pyridine Hydrochloride

Step A: Preparation of N,N-Diethyl furo[2,3-b]pyridine-5-carboxamide

To a suspension of furo[2,3-b]pyridine-5-carboxylic acid (3.30 g, 20.2 mmol) in methylene chloride (80 mL), under a nitrogen atmosphere at room temperature, was added oxalyl chloride (4.2 mL, 48 mmol) and then four drops of dimethylformamide. The reaction mixture was stirred until gas evolution ceased (4–5 hours) and a clear solution resulted. This solution was evaporated in vacuo and the excess oxalyl chloride chased by evaporation with benzene. The residue was dissolved in chloroform (50 mL) and diethylamine (5.2 mL, 50 mmol) was added carefully. After 0.5 hours, the chloroform solution was washed with dilute hydrochloric acid, filtered through a pad of charcoal and evaporated to give crude product (5.49 g). This oil was distilled under vacuum to give purified product (3.62 g, 82% yield), bp: 168°–170° C./1.6 mmHg.

Analysis calculated for $C_{12}H_{14}N_2O_2$: N, 12.84; C, 66.03; H, 6.47. Found: N, 12.89; C, 65.50; H, 6.47.

Step B: Preparation of 5-(Diethylaminomethyl)furo[2,3-b]pyridine

To a solution of N,N-diethyl furo[2,3-b]pyridine-5-carboxamide (3.6 g, 16.5 mmol) in dry tetrahydrofuran (35 mL), under a nitrogen atmosphere, was added 1M borane in THF (52 mL, 52 mmol). This solution was warmed at 60° C. for 2–3 hours and then glacial acetic acid (3 mL, 52 mmol) was carefully added. After 0.5 hours, dilute hydrochloric acid (10%) was added to the reaction and the aqueous layer was separated and made basic with sodium hydroxide solution. The product was extracted into methylene chloride, dried over anhydrous sodium sulfate, filtered through a pad of charcoal and the solvent evaporated to give crude oily product (2.6 g). This material was distilled under vacuum to give purified produt (1.2 g, 36% yield), bp: 120°–121° C./1.5 mmHg. A small portion was treated with ethanolic hydrogen chloride to give the hydrochloride salt which was recrystallized from isopropanol, mp: 206°–208° C.

Analysis calculated for $C_{12}H_{16}N_2O \cdot HCl$: N, 11.64; C, 59.86; H, 7.12. Found: N, 11.44; C, 59.78; H, 7.36.

Step C: Preparation of 2-sulfamoyl-5-(diethylaminomethyl)furo[2,3-b]pyridine Hydrochloride To a solution of 5-(diethylaminomethyl)furo[2,3-b]pyridine (1.19 g, 5.83 mmol) in dry tetrahydrofuran (12 mL), under a nitrogen atmosphere and cooled to −70° C., was added dropwise 1.6M butyl lithium in hexane (4.5 mL, 7.2 mmol) to give a dark amber solution. After 0.75 hours sulfur dioxide gas was bubbled over the reaction surface to give a yellow precipitate. This suspension was warmed to room temperature, diluted with diethyl ether and the precipitated sulfinate salt was isolated by filtration. This salt was partially suspended in water (20 mL) and sodium acetate trihydrate (2.8 g, 20.5 mmol) and hydroxylamine-o-sulfonic acid (1.0 g, 8.8 mmol) were added. After stirring the reaction mixture for 15–20 hours, suspended material was removed by filtration and the solution was made basic with sodium hydroxide/sodium carbonate and the product extracted into ethyl acetate. This extract was dried over anhydrous sodium sulfate, filtered through a pad of charcoal and the solvent evaporated. The residue was triturated with diethyl ether and the purified product (561 mg), mp: 148°–150° C., collected by filtration. This material was treated with ethanolic hydrogen chloride to give a salt which was recrystallized from methanol (508 mg, 27% yield), mp: 238°–240° C.

Analysis calculated for $C_{12}H_{17}N_3O_3S \cdot HCl$: N, 13.14; C, 45.06; H, 5.67. Found: N, 13.20; C, 44.78; H, 5.59.

EXAMPLE 26

2-Sulfamoyl-6-(propylthiomethyl)furo[3,2-c]pyridine

Step A: Preparation of
N,N-Dimethyl-N'-[6-(hydroxymethyl)furo[3,2-c]pyridine-2-sulfonyl]formamidine A suspension of N,N-dimethyl-N'-[6-methyl-5-oxidofuro[3,2-c]pyridine-2-sulfonyl]formamidine (4.24 g, 15 mmol) (from Example 13, Step B) in acetic anhydride (13 mL), under a nitrogen atmosphere was heated at 140° C. for 20 minutes to give an amber solution. This reaction mixture was cooled to 100° C. and 6% hydrochloric acid (30 mL) was added. After stirring at 100° C. for 4 hours, the reaction mixture was poured into saturated sodium carbonate (~100 mL) carefully. The product was extracted into methylene chloride, dried over anhydrous sodium sulfate, filtered through a charcoal pad and evaporated to dryness. This residue was triturated with diethyl ether/methylene chloride to give the product (2.21 g, 52% yield) which was used as is.

Step B: Preparation of
2-sulfamoyl-6-(propylthiomethyl)furo[3,2-c]pyridine

To a solution of triphenylphosphine (3.43 g, 13.1 mmol) in dry tetrahydrofuran (50 mL), cooled below −10° C. and under a nitrogen atmosphere, was added diethyl azodicarboxylate (1.85 ml, 12 mmol). After stirring this solution for 20 minutes, bis(propylmercapto)zinc (1.94 g, 9 mmol) was added in one portion, followed by N,N-dimethyl-N'-[6-(hydroxymethyl)furo[3,2-c]pyridine-2-sulfonyl]formamidine (1.70 g, 6 mmol) in another portion. After stirring for 45 minutes, pyridine (4 mL) was added to this suspension and the mixture was allowed to gradually warm to 0° C. over 4.5 hours. This mixture was diluted with methylene chloride (40 mL) and allowed to stir for an additional hour to give a nearly homogeneous solution. This solution was filtered and the solvent removed by evaporation. The residue was partially dissolved in methanol (30 mL) and 10N sodium hydroxide (5 mL) was added to give a clear solution. This reaction mixture was warmed at 50° C. for 1.5 hours. After cooling the reaction mixture, it was diluted with $H_2O$, filtered through filter aid to remove suspended zinc salts and extracted with chloroform to remove triphenylphosphine oxide. The aqueous solution was acidified and the product extracted exhaustively into ethyl acetate. This solution was dried over anhydrous sodium sulfate, filtered through a charcoal pad and the solvent evaporated. The residue was triturated with methylene chloride to give 1.5 g of nearly pure product. This material was crystallized twice from 1,2-dichloroethane to give pure product (1.21 g, 70% yield), mp: 171°–172° C.

Analysis calculated for $C_{11}H_{14}N_2O_3S_2$: N-9.78, C-46.13, H-4.93. Found: N-9.77, C-45.97, H-4.98.

EXAMPLE 27

2-Sulfamoyl-6-(propylsulfinylmethyl)furo[3,2-c]pyridine

To a solution of 2-sulfamoyl-6-(propylthiomethyl)furo[3,2-c]pyridine (913 mg, 3.19 mmol) in methanol (23 mL) and water (8 mL) was added sodium metaperiodate (906 mg, 4.24 mmol). This mixture was stirred for 4 hours as sodium iodate precipitated from the solution. This precipitate was filtered off and the methanol was evaporated. Sodium chloride was added to the residual aqueous solution and this was exhaustively extracted with ethyl acetate. The extract was dried over anhydrous sodium sulfate, filtered and evaporated. The residue was triturated with diethyl ether/methylene chloride to give 820 mg of product. This material was crystallized from a large volume of ethyl acetate to give pure product (470 mg, 49% yield), mp: 179°–180.5° C. (dec).

Analysis calculated for $C_{11}H_{14}N_2O_4S_2$: N-9,27, C-43.67, H-4.67. Found: N-9.18, C-43.31, H-4.55.

EXAMPLE 28

2-Sulfamoyl-6-(propylsulfonylmethyl)furo[3,2-c]pyridine

To a solution of 2-sulfamoyl-6-(propylthiomethyl)furo[3,2-c]pyridine (454 mg, 1.59 mmol) in ethyl acetate (7 mL) and methanol (5 mL) was added dropwise a solution of 80% pure m-chloroperbenzoic acid (682 mg, 3.17 mmol) in ethyl acetate (5 mL). This addition was monitored by TLC and discontinued when over oxidation to the N-oxide became apparent. The solvents were evaporated and the residue was triturated with diethyl ether to give 407 mg of crude product. This material was digested in hot ethyl acetate, filtered to remove the N-oxide, and concentrated to a small volume. Upon cooling the product crystallized out (338 mg). This material was recrystallized from 1,2-dichloroethane to give pure product (273 mg, 54% yeild), mp: 167°–169° C.

Analysis calculated for $C_{11}H_{14}N_2O_5S_2$: N-8.80, C-41.50, H-4.43. Found: N-8.42, C-41.86, H-4.73.

EXAMPLE 29

2-Sulfamoyl-6-(propylsulfonylmethyl)furo[3,2-c]pyridine-5-oxide

To a solution of 2-sulfamoyl-6-(propylthiomethyl)furo[3,2-c]pyridine (724 mg, 2.53 mmol) in methanol (20 mL) and ethyl acetate (20 mL) there was added in portions 80% pure m-chloroperbenzoic acid (1.59 g, 7.39 mmol). The solution was stirred for 20 hours as product slowly precipitated. The precipitated product was collected and digested in hot methanol to give 599 mg of purified product. This material was recrystallized from hot methanol/ethyl acetate (1:1) to give pure product (520 mg, 61.5% yield), mp: 232°–234° C. (dec).

Analysis calculated for $C_{11}H_{14}N_2O_6S_2$: N-8.38, C-39.51, 1 H-4.22. Found: N-8.43, C-39.64, H-3.94.

EXAMPLE 30

| 2-Sulfamoylfuro[3,2-c]pyridine | 1 mg | 15 mg |
| --- | --- | --- |
| Monobasic sodium phosphate $2H_2O$ | 9.38 mg | 6.10 mg |
| Dibasic sodium phosphate .$12H_2O$ | 28.48 mg | 16.80 mg |
| Benzalkonium chloride | 0.10 mg | 0.10 mg |
| Water for injection q.s. ad. | 1.0 ml | 1.0 ml |

The novel compound, phosphate buffer salts, and benzalkonium chloride are added to and dissolved in water. The pH of the composition is adjusted to 6.8 and diluted to volume. The composition is rendered sterile by ionizing radiation.

EXAMPLE 31

| 2-Sulfamoylfuro[3,2-c]pyridine | 5 mg |
| --- | --- |

| | |
|---|---|
| petrolatum q.s. ad. | 1 gram |

The compound and the petrolatum are aseptically combined.

EXAMPLE 32

| | |
|---|---|
| 4-(2-Hydroxyethyl)amino-2-sulfamoylfuro[3,2-c]pyridine | 1 mg |
| Hydroxypropylcellulose q.s. | 12 mg |

Opthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Opthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

What is claimed is:

1. A compound of the structural formula:

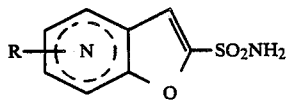

or N-oxide, or an opthalmologically acceptable salt thereof
wherein:

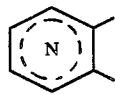

is a pyrido, dihydropyrido or tetrahydropyrido group with the N at the 4-, 5-, 6- or 7-position; and
R is
(1) $C_{1-5}$ alkyl, either straight chain, branched chain or cyclic and either unsubstituted or substituted with hydroxy, amino, $C_{1-5}$ alkylamino or di($C_{1-5}$alkyl)amino, the alkyl groups of which can be joined together to form a 5–7 membered heterocycle,
(2) Hydrogen
(3) —$OR^1$, wherein $R^1$ is hydrogen, $C_{1-5}$ alkyl, amino-$C_{1-3}$ alkyl, $C_{1-3}$ alkylamino-$C_{1-3}$ alkyl, di($C_{1-3}$ alkyl) amino-$C_{1-3}$ alkyl, hydroxy-$C_{1-3}$ alkyl, or $C_{2-4}$ alkanoyl,
(4)

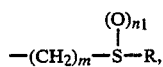

wherein m is 0–3 and n is 0, 1 or 2,
(5) —$N(R^1)_2$ wherein the $R^1$ groups can be the same or different, or joined together to form a 5–7 membered heterocycle (6) halo selected from the group consisting of chloro, bromo and fluoro,
(7) —$NO_2$, or
(8) oxo-; and if

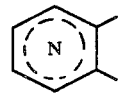

represents a dihydro- or tetrahydropyrido- the N can be substituted with $R^1$ or —$CONH_2$.

2. The compound of claim 1 wherein

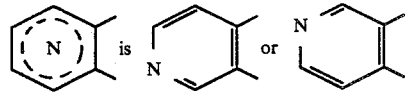

3. The compound of claim 2 wherein R is hydrogen, hydroxy, hydroxy-$C_{1-5}$ alkyl, $C_{1-5}$ alkylamino-$C_{1-5}$ alkyl, or di($c_{1-5}$ alkyl)amino-$C_{1-5}$alkyl.

4. The compound of claim 3, which is:
2-sulfamoyl-4-methoxyfuro[3,2-c]pyridine;
2-Sulfamoylfuro[2,3-c]pyridine;
2-Sulfamoylfuro[3,2-c]pyridine;
2-Sulfamoyl-4-chloro-furo[3,2-c]pyridine;
2-Sulfamoyl-4-(2-hydroxyethylamino)furo[3,2-c]pyridine; or
2-Sulfamoyl-4-[2-(dimethylamino) ethylamino]furo[3,2-c]pyridine; or an opthalmologically acceptable salt thereof.

5. An opthalmological formulation for treating elevated intraocular pressure comprising an ophthalmologically acceptable carrier and an effective intraocular pressure lowering amount of a compound of claim 1 or an ophthalmologically acceptable salt thereof.

6. The formulation of claim 5, wherein

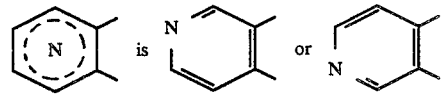

7. The formulation of claim 6, wherein R is hydrogen, hydroxy, hydroxy-$C_{1-5}$ alkyl, $C_{1-5}$alkylamino-$C_{1-5}$alkyl or di($C_{1-5}$alkyl)amino-$C_{1-5}$alkyl.

8. The formulation of claim 7, wherein the compound is:
2-Sulfamoyl-4-methoxyfuro[3,2-c]pyridine;
2-Sulfamoylfuro[2,3-c]pyridine;
2-Sulfamoylfuro[3,2-c]pyridine;
2-Sulfamoyl-4-chloro-furo[3,2-c]pyridine;
2-Sulfamoyl-4-(2-hydroxylethylamino)furo[3,2-c]pyridine; or
2-Sulfamoyl-4-[2-(dimethylamino)ethylamino]furo[3,2-c]pyridine; or an ophthalmologically acceptable salt thereof.

9. A method of treating elevated intraocular pressure which comprises the administration to a patient in need of such treatment of an effective intraocular pressure lowering amount of the compound of claim 1.

10. The method of claim 9, wherein

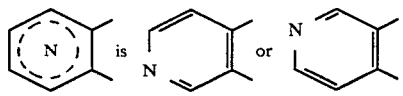

11. The method of claim 10, wherein R is hydrogen, hydroxy, hydroxy-$C_{1-5}$ alkyl, $C_{1-5}$ alkylamino-$C_{1-5}$ alkyl, or di($C_{1-5}$ alkyl)amino-$C_{1-5}$-alkyl.

12. The method of claim 11, wherein the compound is:
2-Sulfamoyl-4-methoxyfuro[3,2-c]pyridine
2-Sulfamoylfuro[2,3-c]pyridine;
2-Sulfamoylfuro[3,2-c]pyridine;
2-Sulfamoyl-4-chloro-furo[3,2-c]pyridine;
2-Sulfamoyl-4-(2-hydroxyethylamino)furo[3,2-c]pyridine; or
2-Sulfamoyl-4-[2-(dimethylamino) ethylamino]furo[3,2-c]pyridine; or an ophthalmologically acceptable salt thereof.

* * * * *